United States Patent [19]

Kleiner et al.

[11] Patent Number: 4,781,722
[45] Date of Patent: Nov. 1, 1988

[54] NOVEL ALKANEPHOSPHONIC MONOESTER SALTS, PREPARATION THEREOF AND USE THEREOF AS SPIN FINISHES FOR TEXTILE FIBERS

[75] Inventors: Hans-Jerg Kleiner, Kronberg/Taunus; Rolf Kleber, Nue-Isenburg; Lothar Jaeckel, Flörsheim am Main, all of Fed. Rep. of Germany

[73] Assignee: Hoechst Aktiengesellschaft, Frankfurt am Main, Fed. Rep. of Germany

[21] Appl. No.: 162,417

[22] Filed: Mar. 1, 1988

[30] Foreign Application Priority Data

Mar. 3, 1987 [DE] Fed. Rep. of Germany ....... 3706784

[51] Int. Cl.$^4$ .................... D06M 1/02; D06M 13/26; C07F 9/40
[52] U.S. Cl. ........................ 8/127.1; 8/196; 260/502.4 R; 260/502.4 P; 558/89; 558/186
[58] Field of Search ................ 8/127.1, 196; 558/186, 558/89

[56] References Cited

U.S. PATENT DOCUMENTS

| | | | |
|---|---|---|---|
| 3,004,056 | 10/1961 | Nunn et al. | 252/174.16 |
| 3,004,057 | 10/1961 | Nunn | 252/174.16 |
| 3,646,133 | 2/1972 | Kerst | 8/127.1 |
| 4,069,245 | 1/1978 | Dursch et al. | 260/502.4 R |

FOREIGN PATENT DOCUMENTS

| | | |
|---|---|---|
| 0029172 | 5/1981 | European Pat. Off. |
| 2758580 | 7/1979 | Fed. Rep. of Germany |
| 1457535 | 12/1976 | United Kingdom |

*Primary Examiner*—A. Lionel Clingman

[57] ABSTRACT

Novel alkanephosphonic monoester salts, preparation thereof and use thereof as spin finishes for textile fibers Alkylphosphonic monoester salts of the formula

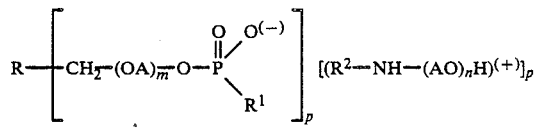

where R, if p=1, is alkyl, and, if p=4, a carbon atom, $R^1$ denotes $C_1$–$C_4$-alkyl, A denotes $C_2H_4$ and/or $C_3H_7$, m denotes a number from 15 to 35, $R^2$ denotes $C_6$–$C_{24}$-alkyl, n denotes a number from 0 to 15, and p denotes 1 or 4. These compounds are suitable for use as spin finishes for textile fibers and are distinguished by very good thermostability.

8 Claims, No Drawings

NOVEL ALKANEPHOSPHONIC MONOESTER SALTS, PREPARATION THEREOF AND USE THEREOF AS SPIN FINISHES FOR TEXTILE FIBERS

DESCRIPTION

Novel alkanephosphonic monoester salts, preparation thereof and use thereof as spin finishes for textile fibers.

The functions of a spin finish include first and foremost the conferring of adequate lubricity during fiber production and also reducing electrostatic charge buildup. Modern processing techniques impose substantial thermal stresses on the spin finish, so that in addition the thermostability of spin finishes is becoming more and more important.

The spin finishing of fibers with anionic compounds for the purpose of reducing electrostatic charge buildup is well known. Phosphoric esters as described in U.S. Pat. Nos. 3,004,056 and 3,004,057, which are obtainable by reaction of $P_2O_5$, polyphosphoric acid or $POCl_3$ with alcohols, are the best-known antistats. However, the products described therein have only limited thermostability and usually contain inorganic phosphate, which presents substantial friction problems.

DT Pat. No. 2,256,835 describes thermostable monoesters of phosphonic acids for spin finishing synthetic fibers. However, the products present substantial problems in synthesis. They are prepared by radical-initiated reaction of long-chain olefins with phosphites. This reaction can give rise to dimers of the olefin, and the subsequent hydrolysis to the phosphonic monoester is a difficult-to-control reaction.

EP Pat. No. 0,029,172, furthermore, describes thermostable monoesters of phosphonic acids of the formula

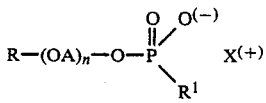

where R denotes straight-chain or branched $C_6$–$C_{22}$-, preferably $C_6$–$C_{16}$-alkyl or -alkenyl, $R^1$ denotes $C_1$–$C_4$-alkyl, A denotes a group of the formula —$CH_2$—$CH_2$— or —$CH_2CHCH_3$, n denotes a number from 1 to 15, preferably from 1 to 8, and X denotes an alkali metal or ammonium ion. These phosphonic monoesters are highly suitable for use as spin finishes for textile fibers. However, their thermostability is not adequate for producing industrial yarns, where temperatures of not less than 200° C. to 350° C. can be reached.

In further refinement of this inventive idea, it has now been found that amine salts of specific phosphonic monoesters have the desired high thermostability.

The invention provides alkanephosphonic monoester salts of the formula

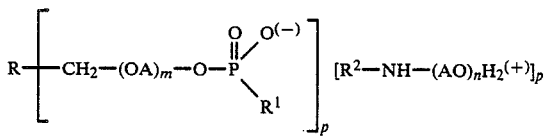

where R, if p=1, is straight-chain or branched $C_1$–$C_7$-alkyl, preferably $C_3$–$C_4$-alkyl, and, if p=4, a carbon atom, $R^1$ denotes $C_1$–$C_4$-alkyl, A denotes $C_2H_4$ and/or $C_3H_7$, m denotes a number from 15 to 35, preferably from 20 to 30, $R^2$ denotes straight-chain or branched $C_6$–$C_{24}$-alkyl, preferably $C_{16}$–$C_{20}$-alkyl, n denotes a number from 0 to 15, preferably from 1 to 8, and p denotes 1 or 4.

The invention further provides the preparation and use of alkanephosphonic monoester salts of the above formula as spin finishes.

These alkanephosphonic monoester salts are preparationwise readily accessible from the corresponding phosphonic anhydrides by reacting these anhydrides of the formula $(R^1—PO_2)_x$ with equimolar amounts of an alkoxylate of an alcohol (cf. Houben-Weyl vol. XIII/1 page 413). The alkoxylated alcohols can have been alkoxylated either only with ethylene oxide or propylene oxide or, however, with a mixture of the two alkylene oxides. Correspondingly, the resulting products of the above formula then contain simultaneously ethylene oxide and propylene oxide groups. The reaction temperature for the alcoholysis of the phosphonic anhydrides is preferably 30°–120° C., in particular 80°–100° C., and the solvents used are inert compounds such as aliphatic or aromatic hydrocarbons, halohydrocarbons, or high ethers. However, it is also possible to use no solvent. If a solvent is used, the esters can be isolated by distilling off the solvent. The alkanephosphonic anhydride starting compounds are readily accessible in various ways (cf. Houben-Weyl, Methoden der org. Chem. [Methods of organic chemistry], Georg Thieme Verlag, Stuttgart, vol. XII/1, page 612, (1963), DE Offenlegungsschrift No. 2,758,580, DE Offenlegungsschrift No. 2,441,878). The anhydrides obtained in this reaction by the process of DE Offenlegungsschrift No. 2,758,580 are likewise usable and preferred. To prepare the salts, the alkanephosphonic monoesters are treated, preferably in the absence of any solvent, with the corresponding amines. Suitable amines of this type are the longer-chain amines such as, for example, octadecylamine. In particular, the ethoxylated longer-chain amines such as, for example, stearylamine with 8 moles of ethylene oxide are suitable for preparing the amine salts according to the invention. If desired, it is also possible to add water as a diluent. The amines are frequently used in above-stoichiometric amounts, for example about 2 moles of amine per mole of monoester. The amount of amine used depends on the pH of a 1% aqueous solution of the amine/amine salt of monoester mixture, which should be about 5.5 to 6.5.

The alkanephosphonic monoester salts are highly thermostable and show pronounced gliding properties and also highly antistatic properties. They are therefore highly suitable for use as spin finishes for textile, in particular industrial, fibers based on polyester, polyamide (including aramids) and polyacrylonitrile. Ceramic fibers also come into consideration. The products can be used solo or, alternatively, combined with other spin finishes, such as, for example, ester or mineral oils, fiber bundle cohesion agents, ethoxylated alcohols or fatty acids, emulsifiers, silicone oils and the like. The addon for the alkanephosphonic ester salts is 0.02–2% by weight, preferably 0.1–1.0% by weight, of active substance. The products can be applied to continuous filaments or staple fibers, to tows and stuffing fibers made of polyester, polyamide, polyacrylonitrile, polyolefins and also natural and regenerated cellulosic fibers, wool or cotton in production and in further, textile processing (secondary spinning). Applied after dyeing, they confer good gliding properties combined with high antistatic effectiveness on the filaments or fibers so finished.

EXAMPLE 1

500 g, about 0.4 mol, of polyglycol B 11/50 (reaction product of butanol with ethylene oxide/propylene oxide in a ratio of 1:1, having a molecular weight of about 1,200) were heated with stirring to 100° C. 88.4 g (0.417 mol) of propanephosphonic anhydride solution (50% strength in dichloromethane) were added dropwise in the course of 2 to 3 hours. This is followed by a further 4 hours of stirring, cooling down to room temperature and applying a vacuum of 0.67 kPa. The temperature was then slowly raised to 100° C. The dichloromethane was collected in a downstream cold trap. After cooling, 544 g (about 0.892 mol) of a reaction product of stearylamine with 8 mol of ethylene oxide were added dropwise with stirring in the course of 2 hours. At the end of the reaction, 1,088.4 g of end product had been obtained.

EXAMPLE 2

500 g (about 0.42 mol) of polyglycol B 11/50 (reaction product of butanol with ethylene oxide/propylene oxide in a ratio of 1:1, having a molecular weight of about 1,200) were heated with stirring to 100° C. 88.4 g (0.417 mol) of propanephosphonic anhydride solution (50% strength in dichloromethane) were added dropwise in the course of 2 to 3 hours. This is followed by a further 9 hours of stirring, cooling down to room temperature and applying a vacuum of 0.67 kPa. The temperature was then slowly raised to 100° C. The dichloromethane was collected in a downstream cold trap. After cooling, 113 g (0.42 mol) of octadecylamine were added with stirring at 30° to 40° C. Stirring was continued for several hours. At the end of the reaction, 657 g of end product had been obtained.

EXAMPLE 3

522 g (about 0.105 mol) of polyglycol P 41/300 (reaction product of pentaerythritol with ethylene oxide/propylene oxide in the ratio of 4:1, having a molecular weight of about 5,000) were heated with stirring to 100° C. 85 g (0.417 mol) of propanephosphonic anhydride solution (52% strength in dichloromethane) were then added dropwise in the course of 2 hours. This is followed by stirring for a further 2 hours and applying a vacuum of 0.67 kPa. The dichloromethane was collected in a downstream cold trap. After cooling, 544 g (about 0.892 mol) of a reaction product of stearylamine with 8 mol of ethylene oxide were added dropwise with stirring. At the end of the reaction, 1,110 g of end product had been obtained.

EXAMPLE 4

Thermostability:

1 g of product (active substance content) is heated at 220° C. for 20 minutes, 1 hour and 2 hours at a time, and the loss due to evaporation is determined gravimetrically.

(a) Potassium salt of mono-2-ethylhexyl propanephosphonate (Example 1 of EP Pat No. 0,029,172)
(b) Example 1 according to the invention
(c) Example 3 according to the invention

|  | 20 min loss | 1 hour loss | 2 hours loss |
|---|---|---|---|
| (a) Comparison | 5% | 12% | 23% |
| (b) | 1% | 4.8% | 10.2% |
| (c) | 1% | 4.0% | 8.5% |

The other values of the products of Examples (b) and (c) in respect of their gliding properties (dynamic and electrostatic friction) and their antistatic effectiveness are satisfactory for processing on industrial yarns.

We claim:

1. An alkylphosphonic monoester salt of the formula

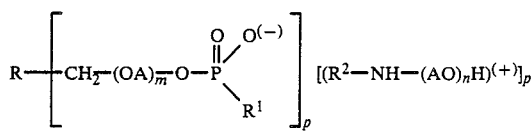

where R, if $p=1$, is straight-chain or branched $C_1$-$C_7$-alkyl, and, if $p=4$, a carbon atom, $R^1$ denotes $C_1$-$C_4$-alkyl, A denotes $C_2H_4$ and/or $C_3H_6$, m denotes a number from 15 to 35, $R^2$ denotes straight-chain or branched $C_6$-$C_{24}$-alkyl, n denotes a number from 0 to 15, and p denotes 1 or 4.

2. A process for preparing an alkanephosphonic monoester salt as claimed in claim 1, which comprises reacting a phosphonic anhydride $(R^1-PO_2)_x$ with an alcohol of the formula

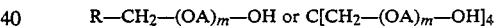

and reacting the resulting alkanephosphonic monoester with an amine of the formula $R^2-NH-(AO)_n-H$.

3. A monoester salt as claimed in claim 1, wherein R, if $p=1$, is $C_3$-$C_4$ alkyl.

4. A monoester salt as claimed in claim 1, wherein m denotes a number from 20 to 30.

5. A monoester salt as claimed in claim 1, wherein $R^2$ denotes $C_{16}$-$C_{20}$ alkyl.

6. A monoester salt as claimed in claim 1, wherein n denotes a number from 1 to 8.

7. A monoester salt as claimed in claim 1, wherein R, if $p=1$, is $C_3$-$C_4$ alkyl; m denotes a number from 20 to 30; $R^2$ denotes $C_{16}$-$C_{20}$ alkyl; and n denotes a number from 1 to 8.

8. A process for providing a spin finish for textile fibers, comprising the step of applying to the fibers a monoester salt as claimed in claim 1.

* * * * *